(12) United States Patent
Ryan et al.

(10) Patent No.: US 10,751,204 B2
(45) Date of Patent: Aug. 25, 2020

(54) DRUG-ELUTING STENT FORMED FROM A DEFORMABLE HOLLOW STRUT FOR A CUSTOMIZABLE ELUTION RATE

(71) Applicant: Medtronic Vascular, Inc., Santa Rosa, CA (US)

(72) Inventors: Cian Ryan, Galway (IE); David Hobbins, Galway (IE); Shane Nolan, Clare (IE); Michael Sayers, Limerick (IE); Eamon Keane, Galway (IE); Brian Dowling, Garristown (IE); Jonathan Cope, Santa Rosa, CA (US); Conor O'Donovan, Galway (IE)

(73) Assignee: Medtronic, Inc., Minneapolis, MN (US)

(*) Notice: Subject to any disclaimer, the term of this patent is extended or adjusted under 35 U.S.C. 154(b) by 216 days.

(21) Appl. No.: 15/617,757

(22) Filed: Jun. 8, 2017

(65) Prior Publication Data

US 2017/0354521 A1    Dec. 14, 2017

Related U.S. Application Data

(60) Provisional application No. 62/348,495, filed on Jun. 10, 2016.

(51) Int. Cl.
*A61F 2/915* (2013.01)
*A61F 2/89* (2013.01)
(Continued)

(52) U.S. Cl.
CPC ............ *A61F 2/915* (2013.01); *A61F 2/89* (2013.01); *A61F 2/958* (2013.01); *A61M 31/002* (2013.01);
(Continued)

(58) Field of Classification Search
CPC ............ A61F 2/915; A61F 2250/0036; A61F 2250/0068
See application file for complete search history.

(56) References Cited

U.S. PATENT DOCUMENTS

| 4,539,226 A | 9/1985 | Paek et al. |
| 4,886,062 A | 12/1989 | Wiktor |
(Continued)

FOREIGN PATENT DOCUMENTS

| EP | 1891995 A1 | 2/2008 |
| WO | 1998/23228 A1 | 6/1998 |
(Continued)

OTHER PUBLICATIONS

U.S. Appl. No. 61/244,049, filed Sep. 20, 2009, Thompson et al.
(Continued)

*Primary Examiner* — Christopher D. Prone
*Assistant Examiner* — Christine L Nelson

(57) ABSTRACT

Methods and apparatus are disclosed for customizing an elution rate of a stent. The stent includes a hollow strut that forms the stent, the hollow strut defining a lumenal space, a drug formulation disposed within the lumenal space of the hollow strut, and at least one side port for eluting the drug formulation in vivo. When the stent is in the radially expanded configuration the hollow strut is deformable from a first configuration that has a first elution rate for the drug formulation to a second configuration that has a second elution rate for the drug formulation. The second elution rate is faster than the first elution rate. The hollow strut deforms from the first configuration to the second configuration upon application of an applied pressure above a predetermined threshold.

20 Claims, 8 Drawing Sheets

(51) Int. Cl.
*A61F 2/958* (2013.01)
*A61M 31/00* (2006.01)

(52) U.S. Cl.
CPC .............. *A61F 2002/91558* (2013.01); *A61F 2002/91575* (2013.01); *A61F 2210/0004* (2013.01); *A61F 2240/002* (2013.01); *A61F 2250/0036* (2013.01); *A61F 2250/0068* (2013.01); *A61M 2205/04* (2013.01)

(56) References Cited

U.S. PATENT DOCUMENTS

| | | | |
|---|---|---|---|
| 5,019,090 | A | 5/1991 | Pinchuk |
| 5,133,732 | A | 7/1992 | Wiktor |
| 5,458,639 | A | 10/1995 | Tsukashima et al. |
| 5,713,949 | A | 2/1998 | Jayaraman |
| 5,782,903 | A | 7/1998 | Wiktor |
| 5,891,507 | A | 4/1999 | Jayaraman |
| 6,136,023 | A | 10/2000 | Boyle |
| 6,203,551 | B1 | 3/2001 | Wu |
| 6,368,658 | B1 | 4/2002 | Schwarz et al. |
| 6,500,147 | B2 | 12/2002 | Omaleki et al. |
| 6,517,889 | B1 | 2/2003 | Jayaraman |
| 6,554,795 | B2 | 4/2003 | Bagaoisan et al. |
| 6,736,827 | B1 | 5/2004 | McAndrew et al. |
| 6,743,462 | B1 | 6/2004 | Pacetti |
| 7,563,324 | B1 | 7/2009 | Chen et al. |
| 7,901,726 | B2 | 3/2011 | McMorrow et al. |
| 8,291,854 | B2 | 10/2012 | Behnisch et al. |
| 8,381,774 | B2 | 2/2013 | Mitchell et al. |
| 8,518,490 | B2 | 8/2013 | Ito et al. |
| 8,668,732 | B2 | 3/2014 | Scheuermann et al. |
| 8,828,474 | B2 | 9/2014 | Mitchell et al. |
| 8,840,660 | B2 | 9/2014 | Weber |
| 9,107,605 | B2 * | 8/2015 | Boyle .................... A61B 5/076 |
| 9,114,032 | B1 | 8/2015 | Pulugurtha |
| 2004/0200729 | A1 | 10/2004 | Boulais et al. |
| 2005/0010282 | A1 | 1/2005 | Thornton et al. |
| 2005/0038504 | A1 | 2/2005 | Halleriet et al. |
| 2005/0074544 | A1 | 4/2005 | Pacetti et al. |
| 2005/0079274 | A1 | 4/2005 | Palasis et al. |
| 2005/0186241 | A1 | 8/2005 | Boyle et al. |
| 2007/0259102 | A1 | 11/2007 | McNiven et al. |
| 2008/0152944 | A1 | 6/2008 | Bonini et al. |
| 2008/0208310 | A1 | 8/2008 | McDermott et al. |
| 2008/0233267 | A1 | 9/2008 | Berglund |
| 2009/0035351 | A1 | 2/2009 | Berglund et al. |
| 2009/0093871 | A1 | 4/2009 | Rea et al. |
| 2009/0143855 | A1 | 6/2009 | Weber et al. |
| 2010/0018602 | A1 | 1/2010 | Chappa |
| 2010/0068404 | A1 | 3/2010 | Wang et al. |
| 2011/0008405 | A1 | 1/2011 | Birdsall et al. |
| 2011/0034992 | A1 | 2/2011 | Papp |
| 2011/0066227 | A1 * | 3/2011 | Meyer ....................... A61F 2/90 623/1.42 |
| 2011/0070357 | A1 | 3/2011 | Mitchell et al. |
| 2011/0264187 | A1 | 10/2011 | Melder |
| 2012/0067008 | A1 | 3/2012 | Bienvenu |
| 2012/0067454 | A1 | 3/2012 | Melder |
| 2012/0070562 | A1 | 3/2012 | Avelar et al. |
| 2012/0216907 | A1 | 8/2012 | Pacetti |
| 2013/0274867 | A1 | 10/2013 | Bienvenu et al. |
| 2014/0163664 | A1 | 6/2014 | Goldsmith |
| 2014/0295093 | A1 | 10/2014 | Hirao |

FOREIGN PATENT DOCUMENTS

| | | |
|---|---|---|
| WO | WO2004/091686 | 10/2004 |
| WO | 2008/134493 A1 | 11/2008 |
| WO | WO2011/008896 | 1/2011 |
| WO | WO2012/036929 | 3/2012 |

OTHER PUBLICATIONS

U.S. Appl. No. 61/244,050, filed Sep. 20, 2009, Silver et al.
U.S. Appl. No. 15/491,138, filed Apr. 19, 2017, Mitchell et al.
U.S. Appl. No. 15/491, 170, filed Apr. 19, 2017, Mitchell et al.
Kim et al. "Electrically Controlled Hydrophobicity in a Surface Modified Nanoporous Carbon" Applied Physics Letters 98, 053106 (2011).
Vallet et al. "Electrowetting of Water and Aqueous Solutions on Poly(ethylene Terephthalate) Insulating Films" Polymer vol. 37, No. 12, pp. 2465-2470, 1996.
PCT/US2017/036604, The International Search Report and the Written Opinion of the International Searching Authority, dated Sep. 8, 2017, 14pgs.
PCT/US2017/036607, The International Search Report and the Written Opinion of the International Searching Authority, dated Sep. 11, 2017, 14pgs.

* cited by examiner

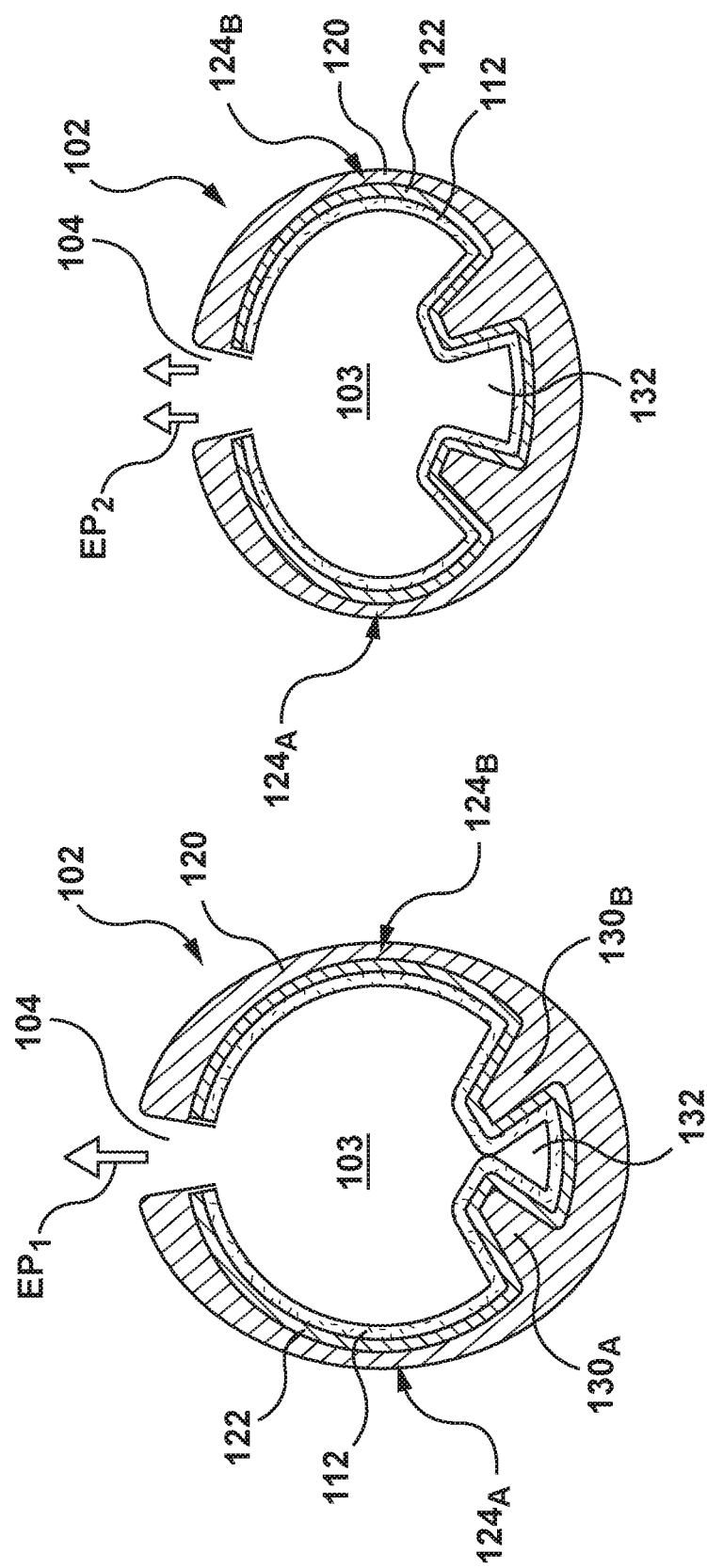

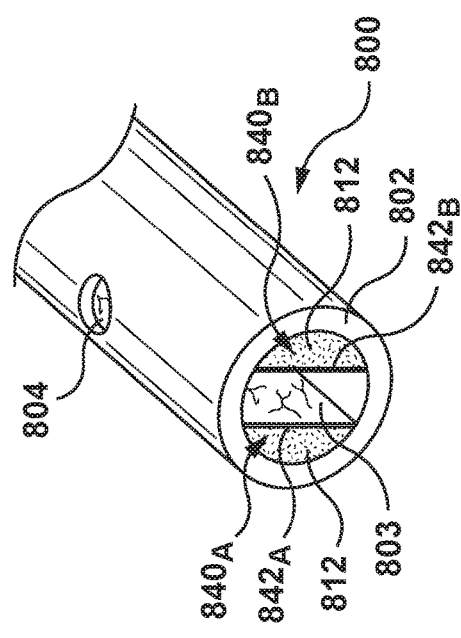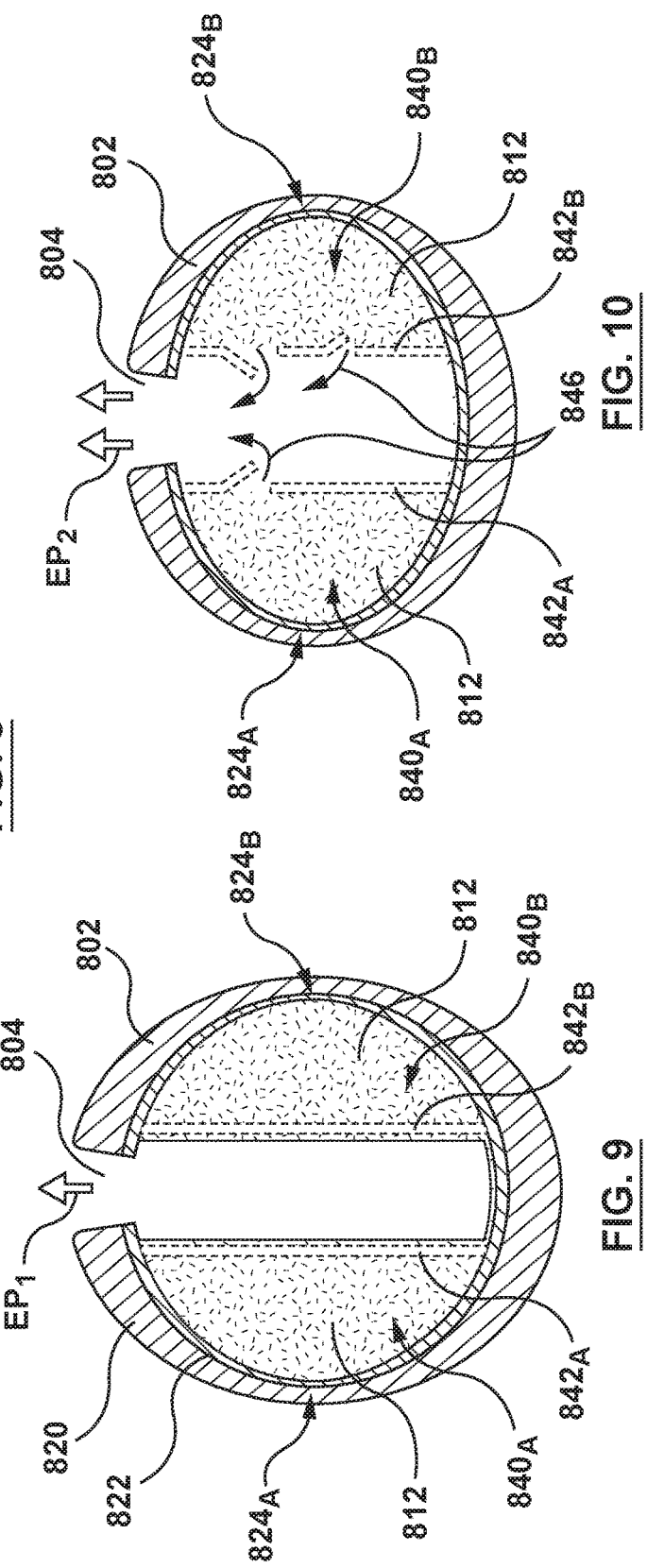

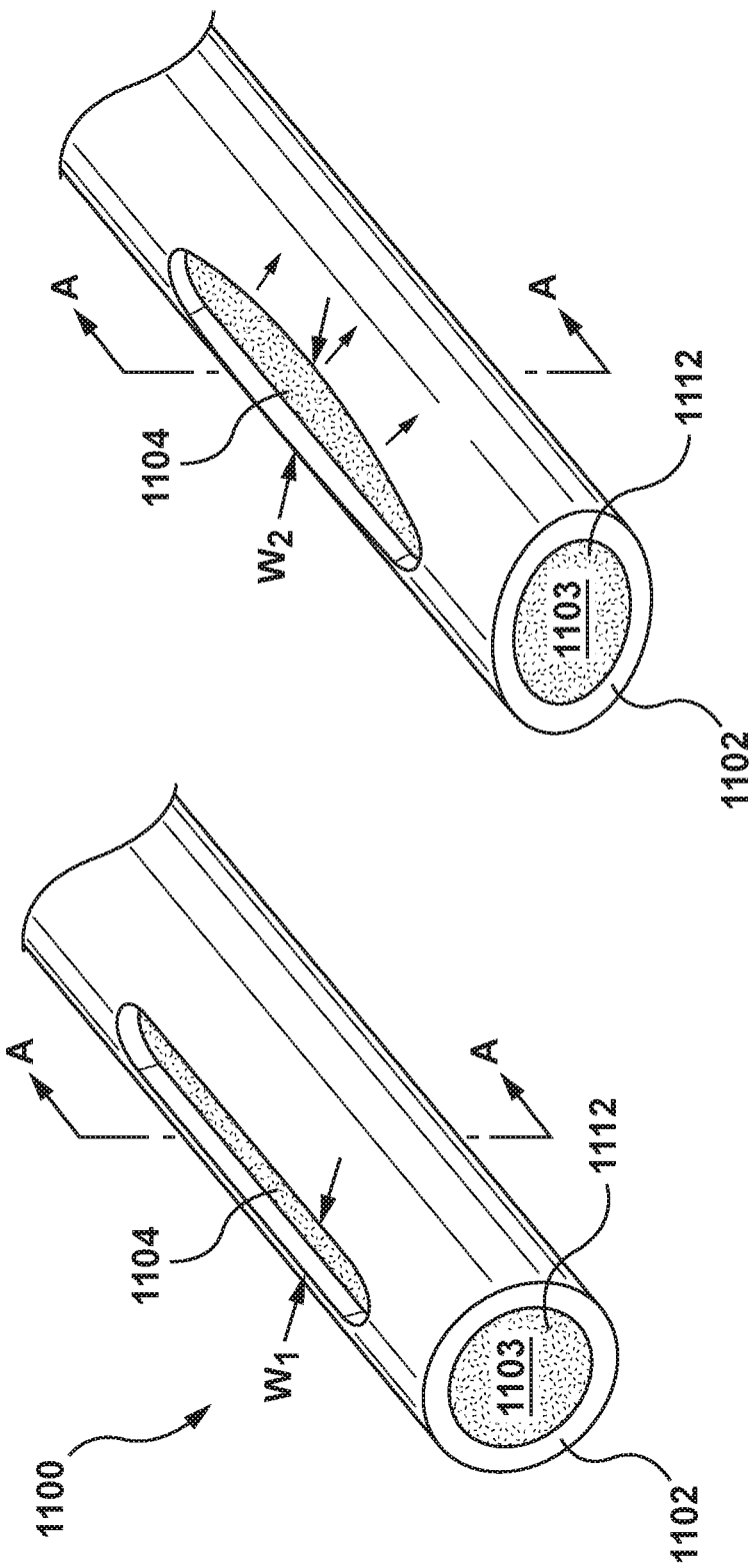

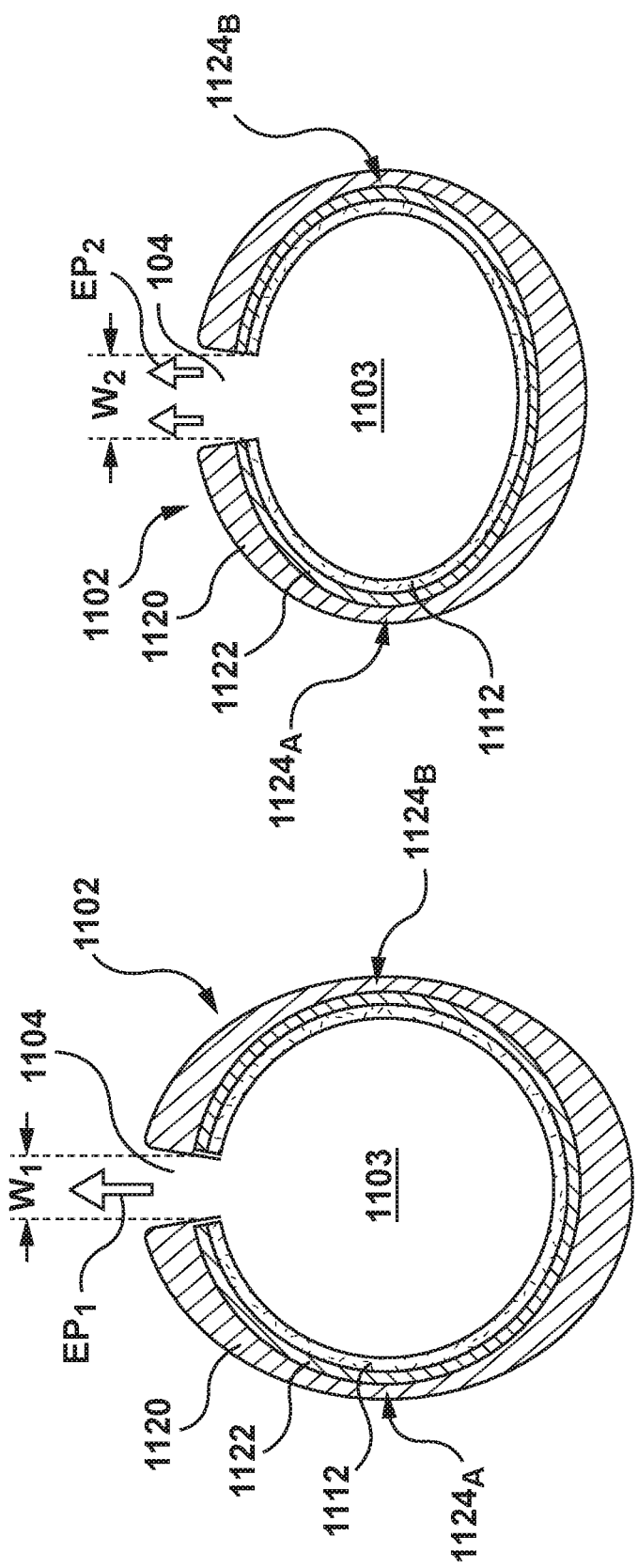

DRUG-ELUTING STENT FORMED FROM A DEFORMABLE HOLLOW STRUT FOR A CUSTOMIZABLE ELUTION RATE

CROSS-REFERENCE TO RELATED APPLICATIONS

This application claims the benefit under 35 U.S.C. § 119(e) of the filing date of U.S. Provisional Application No. 62/348,495, filed Jun. 10, 2016, the contents of which are incorporated by reference herein in their entirety.

FIELD OF THE INVENTION

The invention relates generally to implantable medical devices that release a therapeutic substance or drug, and more particularly to methods of and apparatuses for customizing or tailoring an elution rate or profile of the implantable medical devices.

BACKGROUND OF THE INVENTION

Drug-eluting implantable medical devices are useful for their ability to provide structural support while medically treating the area in which they are implanted. For example, drug-eluting stents have been used to prevent restenosis in coronary arteries. Drug-eluting stents may administer therapeutic agents such as anti-inflammatory compounds that block local invasion/activation of monocytes, thus preventing the secretion of growth factors that may trigger VSMC proliferation and migration. Other potentially anti-restenotic compounds include antiproliferative agents, such as chemotherapeutics, which include sirolimus and paclitaxel. Other classes of drugs such as anti-thrombotics, anti-oxidants, platelet aggregation inhibitors and cytostatic agents have also been suggested for anti-restenotic use.

Drug-eluting medical devices may be coated with a polymeric material which, in turn, is impregnated with a drug or a combination of drugs. Once the medical device is implanted at a target location, the drug is released from the polymer for treatment of the local tissues. The drug is released by a process of diffusion through a polymer layer of a biostable polymer, and/or as the polymer material degrades when the polymer layer is of a biodegradable polymer.

Drug impregnated polymer coatings are limited in the quantity of the drug to be delivered by the amount of a drug that the polymer coating can carry and the size of the medical device. As well, controlling the rate of elution using polymer coatings is difficult.

Accordingly, drug-eluting medical devices that enable increased quantities of a drug to be delivered by the medical device, and allow for improved control of the elution rate of the drug, and improved methods of forming such medical devices are needed. U.S. Patent Application Publication No. 2011/0008405, filed Jul. 9, 2009, U.S. Provisional Application No. 61/244,049, filed Sep. 20, 2009, U.S. Provisional Application No. 61/244,050, filed Sep. 20, 2009, and co-pending U.S. Patent Application Publication No. 2012/0067008, each incorporated by reference herein in their entirety, disclose methods for forming drug-eluting stents with hollow struts. Polymer-free drug-eluting stents formed with hollow struts can achieve similar elution rates as drug-eluting stents with the therapeutic substance disposed in a polymer on the surface of the stent. Polymer-free drug-eluting stents formed with hollow struts achieving similar elution rates as drug-polymer coated stent are expected to have similar clinical efficacy while simultaneously being safer without the polymer coating.

However, it is currently difficult for a physician to customize or tailor the elution rate of a polymer-free drug-eluting stent to meet individual requirements of a specific patient. Accordingly, embodiments hereof relate to methods of and apparatuses to enable a physician to customize or tailor the elution rate of a polymer-free drug-eluting stent.

BRIEF SUMMARY OF THE INVENTION

Embodiments hereof are directed to a stent having a radially compressed configuration for delivery within a vasculature and a radially expanded configuration for deployment within a body lumen. The stent includes a hollow strut that forms the stent, the hollow strut defining a lumenal space. When the stent is in the radially expanded configuration the hollow strut is deformable from a first configuration to a second configuration. A drug formulation is disposed within the lumenal space of the hollow strut, and the stent includes at least one side port for eluting the drug formulation in vivo. The stent has a first elution rate for the drug formulation when the hollow strut is in the first configuration and the stent has a second elution rate for the drug formulation when the hollow strut is in the second configuration. The second elution rate is faster than the first elution rate.

According to another embodiment hereof, the stent includes a hollow strut that forms the stent, the hollow strut defining a lumenal space, a drug formulation disposed within the lumenal space of the hollow strut, and at least one side port for eluting the drug formulation in vivo. When the stent is in the radially expanded configuration the hollow strut is deformable from a first configuration that has a first elution rate for the drug formulation to a second configuration that has a second elution rate for the drug formulation. The second elution rate is faster than the first elution rate. The hollow strut deforms from the first configuration to the second configuration upon application of an applied pressure above a predetermined threshold.

Embodiments hereof are also directed to a method of customizing an elution rate of a stent. A balloon catheter is percutaneously advanced through a vasculature. The balloon catheter has the stent mounted on a balloon of the balloon catheter, and the stent is in a radially compressed configuration during delivery through the vasculature. The stent includes at least one side port for eluting a drug formulation disposed within a lumenal space of a hollow strut that forms the stent. A first elution rate or a second elution rate for the drug formulation is selected in order to customize an elution rate of the stent. The second elution rate is faster than the first elution rate. The first and second elution rates are dependent upon an applied pressure exerted on the hollow strut of the stent such that the first elution rate corresponds to a first configuration of the hollow strut and the second elution rate corresponds to a second configuration of the hollow strut. The hollow strut is configured to deform from the first configuration to the second configuration when the applied pressure is above a predetermined threshold.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 6 is a cross-sectional view of the hollow strut of FIG. 1, the hollow strut being in the first configuration of FIG. 4 such that the stent has a first elution rate.

FIG. 7 is a cross-sectional view of the hollow strut of FIG. 1, the hollow strut being in the second configuration of FIG. 5 such that the stent has a second elution rate, wherein the second elution rate is relatively faster than the first elution rate.

FIG. 8 is a perspective view of a hollow strut for forming a drug eluting stent according to another embodiment hereof, wherein a therapeutic drug is contained within two reservoirs that are formed by two breakable partitions disposed within a lumenal space of the hollow strut.

FIG. 9 is a cross-sectional view of the hollow strut of FIG. 8, the hollow strut being in a first configuration such that the stent has a first elution rate.

FIG. 10 is a cross-sectional view of the hollow strut of FIG. 8, the hollow strut being in a second configuration such that the stent has a second elution rate, wherein the second elution rate is relatively faster than the first elution rate.

FIG. 11 is a perspective view of a hollow strut for forming a drug eluting stent according to another embodiment hereof, the hollow strut being in a first configuration such that the stent has a first elution rate, wherein at least one side port of the hollow strut is an elongated slot.

FIG. 11A is a cross-sectional view taken along line A-A of FIG. 11.

FIG. 12 is a perspective view of the hollow strut of FIG. 11, the hollow strut being in a second configuration such that the stent has a second elution rate, wherein the second elution rate is relatively faster than the first elution rate.

FIG. 12A is a cross-sectional view taken along line A-A of FIG. 12.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Drug eluting stents described herein may be utilized in the context of treatment of blood vessels such as the coronary, carotid and renal arteries, or any other body passageways where it is deemed useful. More particularly, drug eluting stents loaded with a therapeutic substance by methods described herein are adapted for deployment at various treatment sites within the patient, and include vascular stents (e.g., coronary vascular stents and peripheral vascular stents such as cerebral stents), urinary stents (e.g., urethral stents and ureteral stents), biliary stents, tracheal stents, gastrointestinal stents and esophageal stents. In addition, the methods and apparatuses disclosed herein for customizing an elution profile of a stent may also be utilized for customizing an elution profile of any drug eluting medical device that is configured for implantation within or onto the body, including but not limited to staples, other vascular closure medical devices, bone screws, or other implants. Furthermore, there is no intention to be bound by any expressed or implied theory presented in the preceding technical field, background, brief summary or the following detailed description.

Hollow Strut Drug-Eluting Stent

Figure 1:
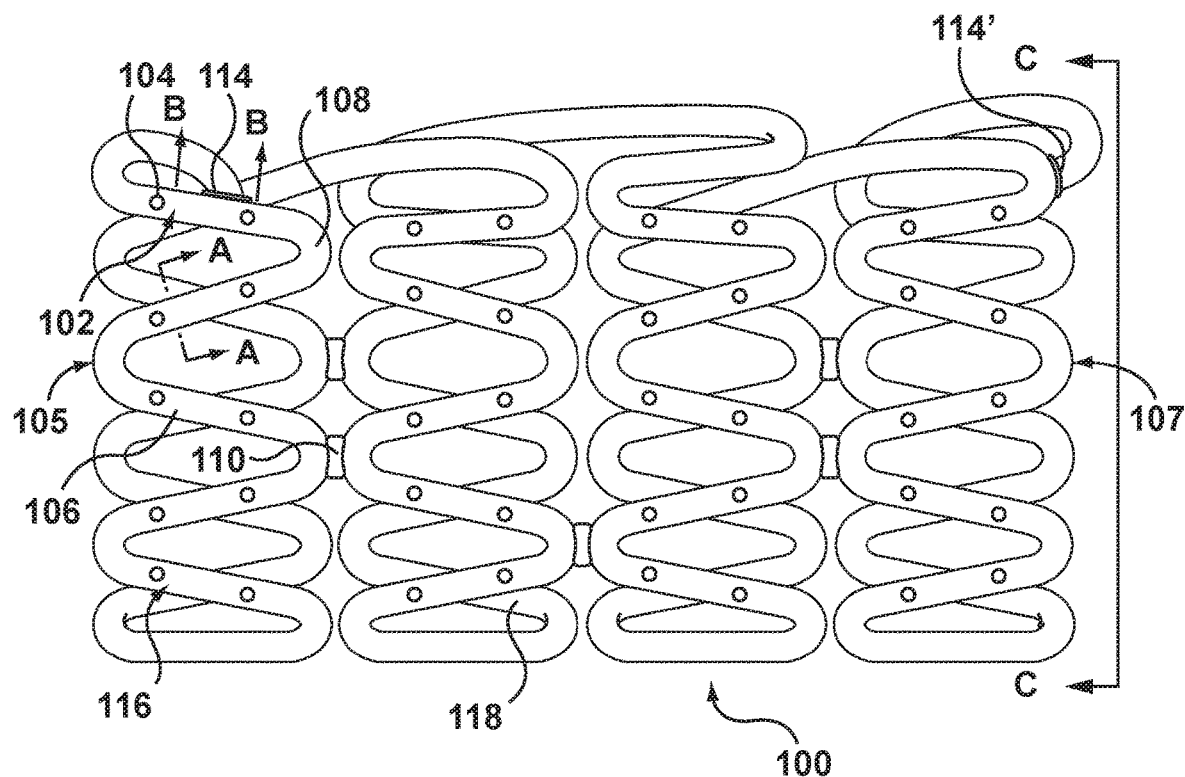
FIG. 1 is a side view of a drug eluting stent formed from a hollow strut according to an embodiment hereof.

An embodiment of a stent 100 to be loaded with a drug in accordance with embodiments hereof is shown in FIGS. 1-7. Referring to FIG. 1, stent 100 is formed from a hollow strut or hollow strut 102 and hereinafter may be referred to as a stent or a hollow core stent. Hollow strut 102 defines a lumen or lumenal space 103, which may be formed before or after being shaped into a desired stent pattern. In other words, as used herein, "a stent formed from a hollow strut" includes a straight hollow wire or strut shaped into a desired stent pattern or a stent constructed from any suitable manufacturing method that results in a tubular component formed into a desired stent pattern, the tubular component having a lumen or lumenal space extending continuously therethrough. As shown in FIG. 1, hollow strut 102 is formed into a series of generally sinusoidal waves including generally straight segments 106 joined by bent segments or crowns 108 to form a waveform that is wound around a mandrel or other forming device to form a generally cylindrical stent 100 that defines a central blood flow passageway or lumen 113 (shown in FIG. 2C) there-through that extends from a first end or tip 105 to a second end or tip 107 of stent 100.

Selected crowns 108 of longitudinally adjacent turns of the waveform may be joined by, for example, fusion points or welds 110 as shown in FIG. 1. Stent 100 is not limited to the pattern shown in FIG. 1. Hollow strut 102 may be formed into any pattern suitable for use as a stent. For example, and not by way of limitation, hollow strut 102 may formed into stent patterns disclosed in U.S. Pat. No. 4,886,062 to Wiktor, U.S. Pat. No. 5,133,732 to Wiktor, U.S. Pat. No. 5,782,903 to Wiktor, U.S. Pat. No. 6,136,023 to Boyle, and U.S. Pat. No. 5,019,090 to Pinchuk, each of which is incorporated by reference herein in its entirety.

Figures 2A, 2B, 2C:
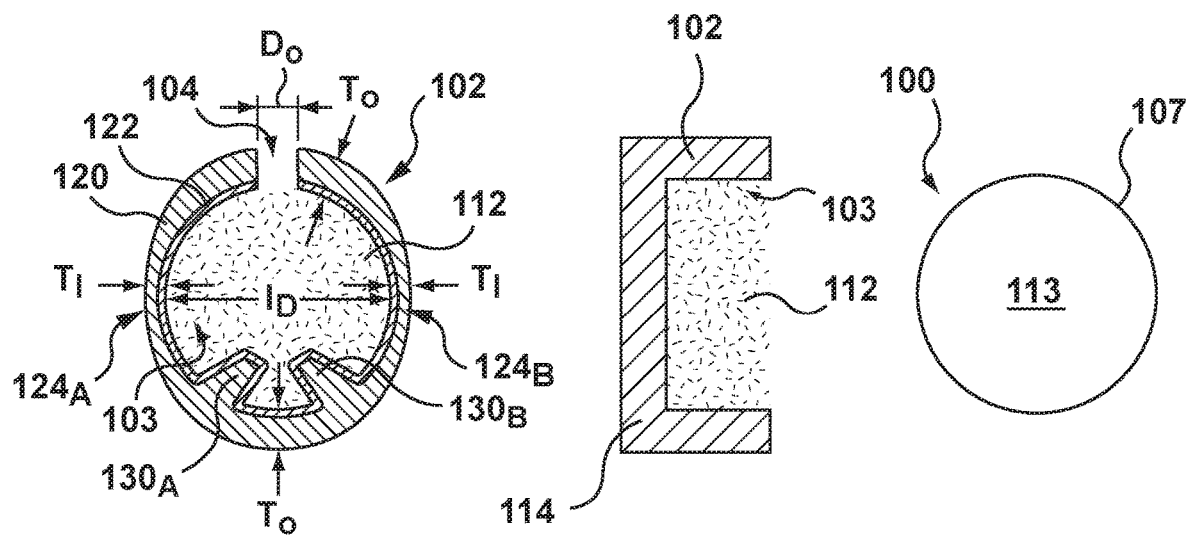
FIG. 2A is a cross-sectional view taken along line A-A of FIG. 1.
FIG. 2B is a sectional view taken along line B-B at an end of the hollow strut of FIG. 1.
FIG. 2C is an end view taken along line C-C of FIG. 1.
Figure 3:
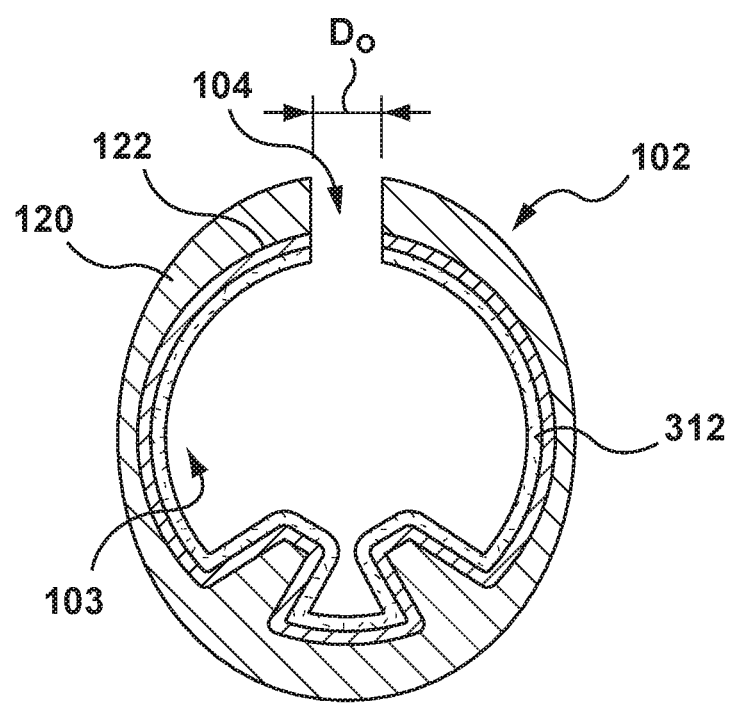
FIG. 3 is a cross-sectional view taken along line A-A of FIG. 1 according to another embodiment hereof.

As shown in FIG. 2A, hollow strut 102 of stent 100 allows for a therapeutic substance or drug 112 to be deposited within lumen or lumenal space 103 of hollow strut 102. Although lumenal space 103 is shown as uniformly filled with therapeutic substance or drug 112 in FIG. 2A, therapeutic substance or drug 112 is not required to fill or be uniformly dispersed within the lumenal space 103 of hollow strut 102 but is only required to occupy at least a portion of the lumenal space. Stated another way, in an embodiment hereof, lumenal space 103 may be intentionally or purposely only partially filled. Further, as shown in the embodiment of FIG. 3, therapeutic substance or drug 112 may be disposed within lumenal space 103 as a layer of film or coating 312 on an inner surface of hollow strut 102. When therapeutic substance or drug 112 is disposed within lumenal space 103 as coating 312, blood enters into lumenal space 103 when stent 100 is implanted in situ. When blood comes into contact with coating 312, elution of therapeutic substance or drug 112 is initiated. Lumenal space 103 continuously extends from a first end 114 to a second end 114' of hollow strut 102. Although hollow strut 102 is shown as generally having a circular cross-section, hollow strut 102 may be generally elliptical or rectangular in cross-section. Hollow strut 102 may have an inner or lumen diameter ID ranging from 0.0005 to 0.02 inch. As used herein, diameter is a transverse measurement of a particular element or component, such as but not limited to hollow strut 102 or side port 104, and the particular element is not required to be circular or spherical in shape.

As best shown in FIG. 2A, hollow strut 102 that forms stent 100 is formed from an outer layer 120 and an inner layer 122. In an embodiment, outer layer 120 is formed from cobalt and inner layer 122 is formed from tantulum. However, outer and inner layers 120, 122 may be made from any suitable metallic materials for providing artificial radial support to the wall tissue, including but not limited to stainless steel, nickel-titanium (nitinol), nickel-cobalt alloy such as MP35N, cobalt-chromium, tantalum, titanium, platinum, gold, silver, palladium, iridium, and the like. Alternatively, hollow strut 102 may be made from a hypotube, which is a hollow metal tube of a very small diameter of the type typically used in manufacturing hypodermic needles. Alternatively, hollow strut 102 may be formed from a non-metallic material, such as a polymeric material. The polymeric material may be biodegradable or bioresorbable such that stent 100 is absorbed in the body after being utilized to restore patency to the lumen and/or provide drug delivery. Hollow strut 102 has a first wall thickness To in the range of 0.0004 to 0.005 inches. However, as will be explained in more detail herein with respect to FIGS. 4-5, the thickness of outer layer 120 varies around the circumference of hollow strut 102 such that hollow strut 102 includes two opposing weakened areas $124_A$, $126_B$ which have a second or relatively thinner wall thickness $T_1$. In an embodiment hereof, first wall thickness To is twice the size of second wall thickness $T_1$ and thus second wall thickness $T_1$ is in the range of 0.0002 to 0.0025 inches.

Hollow strut 102 further includes drug-delivery side openings or ports 104 dispersed along its length to permit therapeutic substance or drug 112 to be released from lumenal space 103. Side ports 104 may be disposed only on generally straight segments 106 of stent 100, only on crowns 108 of stent 100, or on both generally straight segments 106 and crowns 108. Side ports 104 may be sized and shaped as desired to control the elution rate of drug 112 from stent 100. In the embodiment of FIG. 1, side ports 104 are circular holes. However, side ports 104 may be slits or may be holes having any suitable cross-section including but not limited to circular, oval, rectangular, or any polygonal cross-section. Larger sized side ports 104 generally permit a faster elution rate or profile and smaller sized side ports 104 generally provide a slower elution rate or profile. Further, the size and/or quantity of side ports 104 may be varied along stent 100 in order to vary the quantity and/or rate of drug 112 being eluted from stent 100 at different portions of stent 100. Side ports 104 may, for example and not by way of limitation, have a diameter Do that ranges 5-30 µm in width or diameter. Side ports 104 may be provided only on an outwardly facing or ablumenal surface 116 of stent 100, as shown in FIG. 2, only on the inwardly facing or lumenal surface 118 of stent 100, on both surfaces, or may be provided anywhere along the circumference of hollow strut 102.

In various embodiments hereof, a wide range of therapeutic agents or drugs may be utilized as the elutable therapeutic substance or drug 112 contained in lumenal space 103 of hollow strut 102, with the pharmaceutically effective amount being readily determined by one of ordinary skill in the art and ultimately depending, for example, upon the condition to be treated, the nature of the therapeutic agent itself, the tissue into which the dosage form is introduced, and so forth. Further, it will be understood by one of ordinary skill in the art that one or more therapeutic substances or drugs may be loaded into hollow strut 102. Therapeutic substance or drug 112 delivered to the area of a stenotic lesion can be of the type that dissolves plaque material forming the stenosis or can be an anti-platelet formation drug, an anti-thrombotic drug, or an anti-proliferative drug. Such drugs can include TPA, heparin, urokinase, sirolimus or analogues of sirolimus, for example. Of course stent 100 can be used for delivering any suitable medications to the walls and interior of a body vessel including one or more of the following: anti-thrombotic agents, anti-proliferative agents, anti-inflammatory agents, anti-migratory agents, agents affecting extracellular matrix production and organization, antineoplastic agents, antimitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

In accordance with embodiments hereof, stent 100 is loaded or filled with therapeutic substance or drug 112 prior to implantation into the body. Therapeutic substance or drug 112 is generally mixed with a solvent or dispersion medium/dispersant in order to be loaded into lumenal space 103 of hollow strut 102. In addition, the therapeutic substance or drug 112 can be mixed with an excipient to assist with elution in addition to the solvent or dispersion medium/dispersant in order to be loaded into lumenal space 103 of hollow strut 102. Hereinafter, the term "drug formulation" may be used to refer generally to therapeutic substance or drug 112, a solvent or dispersion medium, and any excipients/additives/modifiers added thereto. In one embodiment, therapeutic substance or drug 112 is mixed with a solvent or solvent mixture as a solution before being loaded into hollow strut 102. A solution is a mixture in which therapeutic substance or drug 112 dissolves within a solvent or a solvent mixture. In one embodiment, a solution includes a high-capacity solvent which is an organic solvent that has a high capacity to dissolve therapeutic substance or drug 112. High capacity as utilized herein is defined as an ability to dissolve therapeutic substance or drug 112 at concentrations faster than 500 mg of substance per milliliter of solvent. Examples of high capacity drug dissolving solvents for sirolimus and similar substances include but are not limited to tetrahydrofuran (THF), di-chloromethane (DCM), chloroform, and di-methyl-sulfoxide (DMSO). In addition to the high-capacity solvent, a solution may include an excipient to assist in drug elution. In one embodiment, an excipient may be a surfactant such as but not limited to sorbitan fatty acid esters such as sorbitan monooleate and sorbitan monolaurate, polysorbates such as polysorbate 20, polysorbate 60, and polysorbate 80, cyclodextrins such as 2-hydroxypropyl-beta-cyclodextrin and 2,6-di-O-methyl-beta-cyclodextrin, sodium dodecyl sulfate, octyl glucoside, and low molecular weight poly(ethylene glycol)s. In another embodiment, an excipient may be a hydrophilic agent such as but not limited to salts such as sodium chloride and other materials such as urea, citric acid, and ascorbic acid. In yet another embodiment, an excipient may be a stabilizer such as but not limited to butylated hydroxytoluene (BHT). Depending on the desired drug load, a low capacity solvent can also be chosen for its decreased solubility of therapeutic substance or drug 112. Low capacity is defined as an ability to dissolve therapeutic substance or drug 112 at concentrations typically below 500 mg of drug per milliliter solvent. Examples of low capacity drug dissolving solvents for sirolimus and similar substances include but are not limited to methanol, ethanol, propanol, acetonitrile, ethyl lactate, acetone, and solvent mixtures like tetrahydrofuran/water (9:1 weight ratio). After a solution is loaded into stent 100, therapeutic substance or drug 112 may be precipitated out of the solution, e.g., transformed into solid phase, and the majority of the residual solvent and any nonsolvent, if present, may be extracted from the lumenal space of hollow strut 102 such that primarily only therapeutic substance or drug 112 or therapeutic substance or drug 112 and one or more excipients remain to be eluted into the body.

In another embodiment, therapeutic substance or drug 112 is mixed with a dispersion medium as a slurry/suspension before being loaded into hollow strut 102. In a slurry/suspension form, therapeutic substance or drug 112 is not dissolved but rather dispersed as solid particulate in a dispersion medium, which refers to a continuous medium in liquid form within which the solid particles are dispersed. Examples of dispersion mediums with an inability to dissolve therapeutic substance or drug 112 depend on the properties of therapeutic substance or drug 112. For example, suitable dispersion mediums with an inability to dissolve sirolimus include but are not limited to water, hexane, and other simple alkanes, e.g., C5 thru C10. Certain excipients, suspending agents, surfactants, and/or other additives/modifiers can be added to the drug slurry/suspension to aid in suspension and stabilization, ensure an even dispersion of drug throughout the suspension and/or increase the surface lubricity of the drug particles. Surfactants thus generally prevent therapeutic substance or drug 112 from floating on the top of or sinking to the bottom of the dispersion medium and also prevent particles of therapeutic substance of therapeutic substance or drug 112 from clumping. Examples of surfactants include but are not limited to sorbitan fatty acid esters such as sorbitan monooleate and sorbitan monolaurate, polysorbates such as polysorbate 20, polysorbate 60, and polysorbate 80, and cyclodextrins such as 2-hydroxypropyl-beta-cyclodextrin and 2,6-di-O-methyl-beta-cyclodextrin. In one embodiment, the targeted amount of therapeutic substance or drug 112 is suspended in the dispersion medium and the appropriate additive/modifier is added on a 0.001 to 10 wt % basis of total formulation. In addition, an excipient such as urea or 2,6-di-O-methyl-beta-cylcodextrin may be added to the slurry/suspension to assist in drug elution.

Open ends 114, 114' of hollow strut 102 may be closed or sealed either before or after the drug is loaded within lumenal space 103 as shown in the sectional view of FIG. 2B, which is taken along line 2B-2B of FIG. 1. Once positioned inside of the body at the desired location, stent 100 is deployed for permanent or temporary implantation in the body lumen such that therapeutic substance or drug 112 may elute from lumenal space 103 via side ports 104.

Figure 5:
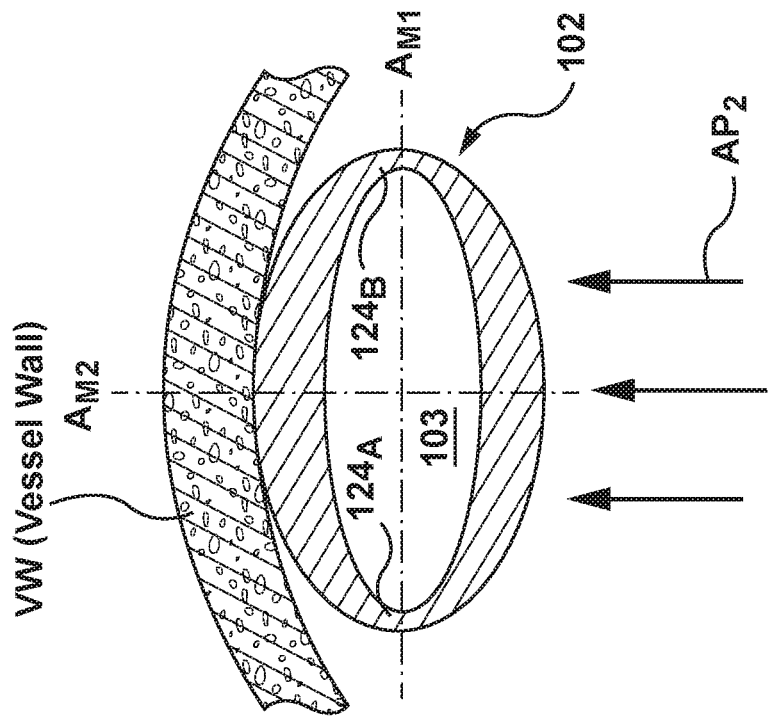
FIG. 5 is a simplified cross-sectional view illustrating the hollow strut of the drug elution stent of FIG. 1 being subjected to a second applied pressure in vivo against a vessel wall, the second applied pressure being higher than the first applied pressure and above the predetermined threshold, wherein the hollow strut is in a second configuration.
Figure 4:
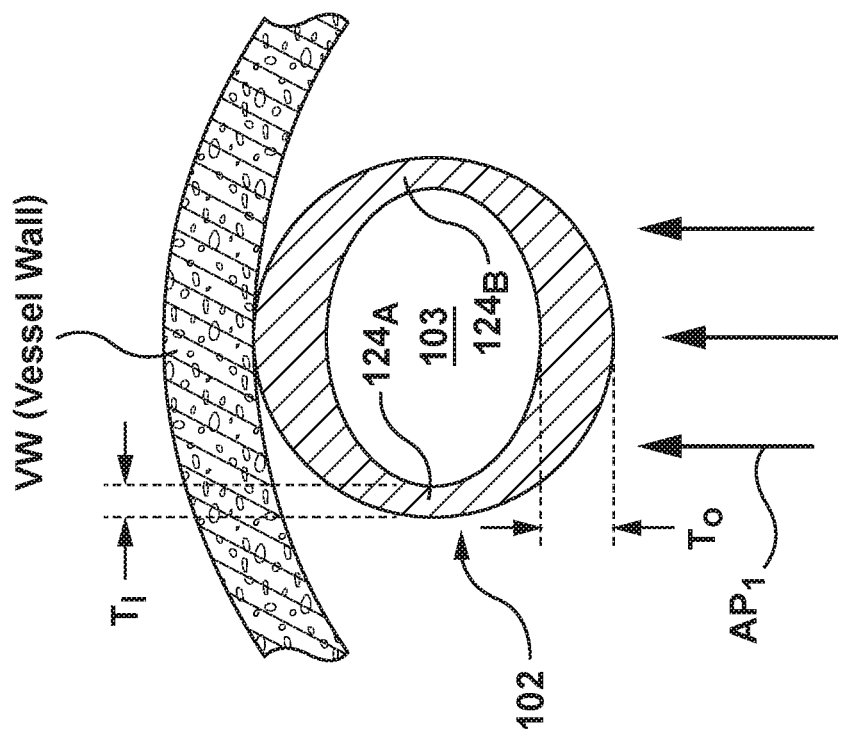
FIG. 4 is a simplified cross-sectional view illustrating the hollow strut of the drug elution stent of FIG. 1 being subjected to a first applied pressure in vivo against a vessel wall, the first applied pressure being below a predetermined threshold, wherein the hollow strut is in a first configuration.

As stated above, the thickness of outer layer 120 varies around the circumference of hollow strut 102 such that hollow strut 102 includes two opposing weakened areas $124_A$, $126_B$ which have a second or relatively thinner wall thickness $T_1$. FIG. 4 is a simplified cross-sectional view illustrating hollow strut 102 of stent 100 being subjected to a first applied pressure $AP_1$ in vivo against a vessel wall VW. First applied pressure $AP_1$ is below a predetermined threshold. In an embodiment hereof, the predetermined threshold is 12 atm and the first applied pressure $AP_1$ is in a range between 10 and 11.9 atm. When the balloon of the balloon catheter is inflated to first applied pressure $AP_1$, the balloon expands stent 100 to the radially expanded or deployed configuration and hollow strut 102 is in a first configuration. In the embodiment of FIG. 4, the first configuration of hollow strut 102 is generally circular. However, hollow strut 102 is deformable when subjected to higher pressures due to opposing weakened areas $124_A$, $124_B$. As stent 100 is deployed or expanded, the applied higher pressure on hollow strut 102 resulting from being sandwiched between the vessel wall and the balloon causes hollow strut 102 to deform. More particularly, opposing weakened areas $124_A$, $124_B$ of relatively thinner dimensions than the remaining circumference of hollow strut 102 configure or permit hollow strut 102 to transform from the first configuration of FIG. 4 to a second configuration of FIG. 5 upon application of an applied pressure above the predetermined threshold. FIG. 5 is a simplified cross-sectional view illustrating hollow strut 102 of stent 100 being subjected to a second applied pressure $AP_2$ in vivo against vessel wall VW. Second applied pressure $AP_2$ is higher than first applied pressure $AP_1$ and is above the predetermined threshold. In an embodiment hereof, the predetermined threshold is 12 atm and the second applied pressure $AP_1$ is in a range between 12.1 and 18 atm. When the balloon of the balloon catheter is inflated to second applied pressure $AP_2$, the balloon expands stent 100 to the radially expanded or deployed configuration and hollow strut 102 is in the second configuration. In the embodiment of FIG. 5, the second configuration of hollow strut 102 is generally elliptical having a minor axis $A_{M2}$ and a major axis $A_{M1}$. However, in another embodiment, the first configuration of hollow strut 102 may be generally elliptical and the second configuration of hollow strut 102 may also be generally elliptical, with the ellipse of the second configuration of hollow strut 102 having a shorter minor axis $A_{M2}$ and/or a longer major axis $A_{M1}$ than the ellipse of the first configuration of hollow strut 102. Stated another way, if both the first and second configurations of hollow strut 102 are generally elliptical, hollow strut 102 as well as lumenal space 103 defined thereby is flattened, squashed, or otherwise compressed when in the second configuration compared to the first configuration. Hollow strut 102 of stent 100 is thus predictably deformable and configured to change shape based on different applied balloon pressures as stent 100 is deployed.

In the simplified cross-sectional views of FIGS. 4-5, certain details of hollow strut 102 are not shown or omitted for sake of clarity and purposes of illustration only. For example, therapeutic substance or drug 112 and side port 104 are not shown on FIGS. 4-5. In addition, outer and inner layers 120, 122 of hollow strut 102 are not delineated on FIGS. 4-5. Further, most notably, raised pillars $130_A$, $130_B$ (which are described in more detail with respect to FIGS. 6-7 herein) are omitted from the simplified illustrations of FIGS. 4-5 because the content of FIGS. 4-5 is equally applicable to all embodiments described herein, including embodiments that do not include raised pillars $130_A$, $130_B$.

As will be explained in more detail herein with respect to FIGS. 13-15, stent 100 has a radially compressed or unexpanded configuration sufficient for delivery to the treatment site within a catheter-based delivery system or other minimally invasive delivery system and a radially expanded or deployed configuration in which stent 100 comes into contact with the vessel. In an embodiment hereof, stent 100 is balloon-expandable. Stent 100 is collapsed or crimped to the radially compressed or unexpanded configuration around the balloon of a balloon catheter for delivery to a treatment site, such as the type of balloon used in an angioplasty procedure. The first applied pressure $AP_1$, which is below the predetermined threshold as explained above, is utilized to expand the balloon. As the balloon expands and exerts the first applied pressure $AP_1$, it physically forces stent 100 to radially expand such that the outside surface of stent 100 comes into contact with the vessel wall. Upon deployment against the vessel wall, hollow strut 102 is in the first configuration described with respect to FIG. 4 above. If it is desired to deform hollow strut 102 to be in the second configuration described with respect to FIG. 5 above, second applied pressure $AP_2$ which is above the predetermined threshold as explained above is utilized to expand the balloon. Once hollow strut 102 is in the desired configuration, the balloon is then collapsed and the balloon catheter is removed, leaving stent 100 in the radially expanded or deployed configuration. Conventional balloon catheters that may be used in the present invention include any type of catheter known in the art, including over-the-wire catheters, rapid-exchange catheters, core wire catheters, and any other appropriate balloon catheters. For example, conventional balloon catheters such as those shown or described in U.S. Pat. Nos. 6,736,827, 6,554,795, 6,500,147, and 5,458,639, which are incorporated by reference herein in their entirety, may be used as the delivery system for stent 100.

In another embodiment hereof, stent 100 may be self-expanding. The term "self-expanding" is used in the following description is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well, poly L-D lactic copolymer, oligo caprylactone copolymer and poly cyclo-octine can be used separately or in conjunction with other shape memory polymers. If self-expanding, stent 100 is collapsed or crimped to the radially compressed or unexpanded configuration inside an outer sheath at the tip of a catheter for delivery to a treatment site as known in the art. Once the catheter is positioned as desired, the outer sheath is retracted thereby allowing stent 100 to self-expand. Upon deployment against the vessel wall, hollow strut 102 is in the first configuration described with respect to FIG. 4 above. After stent 100 is deployed and implanted at the treatment site, a physician may subsequently deliver a balloon catheter and radially expand the balloon thereof to exert second applied pressure $AP_2$ on deployed stent 100 if it is desired to deform hollow strut 102 to be in the second configuration described with respect to FIG. 5 above.

Customizable Elution Rate of Stent 100

Embodiments hereof relate to customizing or tailoring the elution rate of stent 100 to meet individual requirements of a specific patient. The elution rate determines how quickly or slowly therapeutic substance or drug 112 (or therapeutic drug 312 when applied as a coating) will elute from stent 100 in vivo. With hollow strut 102 of stent 100 being predictably deformable based on different applied pressures, a physician is able to control the applied pressure during deployment of stent 100 which in turn controls the elution rate of stent 100. Stated another way, stent 100 is configured to permit a physician to select an elution rate of stent 100 in order to meet individual requirements of a specific patient. For example, diabetic patients or patients with an upcoming surgery require a relatively fast and/or short elution rate while high risk patients require a relatively slow and/or long elution rate. More particularly, a physician may select a first or slower elution rate for therapeutic substance or drug 112, 312 by applying the first applied pressure $AP_1$ to stent 100 during balloon inflation or the physician may select a second or faster elution rate for therapeutic substance or drug 112, 312 by applying the second applied pressure $AP_2$ to stent 100 during balloon inflation to thereby customize the elution rate of stent 100.

In the embodiment of FIGS. 1-7, stent 100 has a customizable elution rate of stent 100 due to raised columns or pillars disposed on an inner surface of hollow strut 102. The raised pillars dictate or control the amount of exposed inner surface of hollow strut 102, which thereby dictates or controls the amount of therapeutic substance or drug 112 that is elutable out of side port 104. By altering the amount of therapeutic substance or drug 112 that can elute out of side port 104, the elution rate of stent 100 can be tailored to suit the individual needs of the patient. In general, larger amounts of therapeutic substance or drug 112 being elutable out of side port 104 generally permit a faster elution rate and smaller amounts of therapeutic substance or drug 112 being elutable out of side port 104 generally provide a slower elution rate.

More particularly, with reference to FIGS. 6-7, a first raised pillar $130_A$ is disposed on the inner surface of hollow strut 102 and a second raised pillar $130_B$ is disposed on the inner surface of hollow strut 102. First and second raised pillars $130_A$, $130_B$ may be integrally formed with hollow strut 102 via an extrusion process. In an embodiment, first and second raised pillars $130_A$, $130_B$ continuously extend from first end 114 to second end 114' of hollow strut 102. In another embodiment, first and second raised pillars $130_A$, $130_B$ continuously extend in a longitudinal direction but do not extend the full length of hollow strut 102. In another embodiment, hollow strut 102 may include a plurality of first and second raised pillars that are discontinuous or spaced apart from each other along the length of hollow strut 102. FIG. 6 is a cross-sectional view of hollow strut 102 being in the first configuration described above with respect to FIG. 4. Stent 100 has a first elution rate or profile $EP_1$ for therapeutic substance or drug 112 when hollow strut 102 is in the first configuration. First and second raised pillars $130_A$, $130_B$ are disposed adjacent to each other when hollow strut 102 is in the first configuration. When first and second raised pillars $130_A$, $130_B$ are adjacent to each other, a pocket 132 of the inner surface of hollow strut 102 is obstructed or blocked and thus therapeutic substance or drug 112 disposed within pocket 132 cannot elute out of side port 104. As used herein, "adjacent to each other" includes pillars that are in contact with each other or only slightly spaced apart such that pocket 132 of the inner surface of hollow strut 102 is enclosed by the pillars in order to contain, obstruct, or otherwise block therapeutic substance or drug 112 from being eluted out of side port 104. Pocket 132 is defined by pillars $130_A$, $130_B$. If first and second raised pillars $130_A$, $130_B$ are elongated (i.e., continuously extend in a longitudinal direction a full length or a portion of the full length of hollow strut 102), pocket 132 correspondingly is elongated and extends in a longitudinal direction. If hollow strut 102 includes a plurality of first and second raised pillars that are discontinuous or spaced apart from each other, each pair of pillars define a pocket and thus hollow strut 102 includes a plurality of discontinuous or spaced apart pockets. The remaining (circumferential) inner surface of hollow strut 102 is not obstructed and thus can elute out of side port 104. In the embodiment of FIG. 6, approximately 75% of the inner surface of hollow strut 102 is exposed and not obstructed while approximately 25% of the inner surface (within pocket 132) is obstructed.

FIG. 7 is a cross-sectional view of hollow strut 102 being in the second configuration of FIG. 5. Stent 100 has a second elution rate or profile $EP_2$ for therapeutic substance or drug 112 when hollow strut 102 is in the second configuration. The second elution rate $EP_2$ is relatively faster than the first elution rate $EP_1$. First and second raised pillars $130_A$, $130_B$ spaced apart from each other when hollow strut 102 is in the second configuration. As hollow strut 102 deforms from the first configuration to the second configuration due to the higher applied pressure above the predetermined threshold, first and second raised pillars $130_A$, $130_B$ move apart within lumenal space 103 of hollow strut 102, thereby increasing the exposed inner surface of hollow strut 102 (as well as the exposed amount of therapeutic substance or drug 112 disposed on the inner surface of hollow strut 102). When first and second raised pillars $130_A$, $130_B$ are spaced apart from each other, pocket 132 of the inner surface of hollow strut 102 is no longer obstructed or blocked and thus therapeutic substance or drug 112 disposed on or within pocket 132 can elute out of side port 104. In the embodiment of FIG. 7, 100% of the inner surface of hollow strut 102 is exposed and not obstructed.

Although FIGS. 6-7 illustrate therapeutic substance or drug 112 disposed within lumenal space 103 of hollow strut 102 as a coating on an inner surface of the hollow strut, therapeutic substance or drug 112 could also fill or partially fill the lumenal space as shown in FIG. 2A.

In addition, although only two configurations of hollow strut 102 are described herein with two corresponding elution rates for the embodiment of FIGS. 1-7, additional intermediate configurations of hollow strut 102 with corresponding intermediate elution rates are possible. Stated another way, hollow strut 102 may be configured to deform in a step-wise manner between the first configuration of FIG. 4 and the second configuration of FIG. 5 in order to interpolate the elution rate in a corresponding step-wise manner between the first elution rate $EP_1$ and the second elution rate $EP_2$. For example, hollow strut 102 may be configured to deform to an intermediate or third configuration in which approximately 90% of the inner surface of hollow strut 102 is exposed and not obstructed while approximately 10% of the inner surface (within pocket 132) is obstructed when a predetermined pressure is applied. In this example, the predetermined pressure would fall somewhere between first applied pressure $AP_1$ and second applied pressure $AP_2$. In an embodiment of this example, hollow strut 102 may be configured to deform to the intermediate or third configuration described above upon exertion of applied pressures between 12.1 and 15 atm and further deform to the second configuration upon exertion of applied pressure between 15 and 18 atm. As such, additional configurations of hollow strut 102 and corresponding elution rates are contemplated.

FIGS. 8-10 illustrate another embodiment of a stent 800 having a hollow strut 802 configured to predictably deform in order to achieve different elution rates. More particularly, FIG. 8 is a perspective view of hollow strut 802 for forming stent 800. The construction of stent 800 and construction of hollow strut 802 is similar to the construction of stent 100 and hollow strut 102, respectively. Stent 800 includes at least one side port 804 for eluting a therapeutic drug 812 disposed within a lumenal space 803 of hollow strut 802 that forms the stent. Further, similar to hollow strut 102, hollow strut 802 is formed from an outer layer 820 and an inner layer 822 (best shown in FIGS. 9-10) and two opposing weakened areas $824_A$, $826_B$ (also shown in FIGS. 9-10) which have a second or relatively thinner wall thickness. However, in this embodiment, the pillars are not present and rather therapeutic drug 812 is contained within two opposing reservoirs $840_A$, $840_B$ that are respectively formed by two breakable or temporary partitions $842_A$, $842_B$ disposed within lumenal space 803 of hollow strut 802. Breakable partitions $842_A$, $842_B$ dictate or control the amount of therapeutic drug 812 that is elutable out of side port 804 because the partitions are configured to break and thereby release more therapeutic drug 812 and thereby result in faster elution rates. By altering the amount of therapeutic drug 812 that can elute out of side port 804, the elution rate of stent 800 can be tailored to suit the individual needs of the patient. In general, larger amounts of therapeutic drug 812 being elutable out of side port 804 generally permit a faster elution rate and smaller amounts of therapeutic drug 812 being elutable out of side port 804 generally provide a slower elution rate.

More particularly, each reservoir $840_A$, $840_B$ is formed by a portion of the inner surface of hollow strut 802 and a respective breakable partition $842_A$, $842_B$. Each breakable partition $842_A$, $842_B$ is formed by a thin brittle layer of a material. In an embodiment, each breakable partition $842_A$, $842_B$ is formed from a harder, brittle form of therapeutic drug 812 or a different therapeutic drug. In another embodiment, each breakable partition $842_A$, $842_B$ is formed from a biodegradable polymer. Each breakable partition $842_A$, $842_B$ is configured to fracture, buckle, crack, or otherwise break upon application of an applied pressure above the predetermined threshold. FIG. 9 is a cross-sectional view of hollow strut 802 being in a first configuration that is similar to the first configuration described above with respect to FIG. 4 in which the hollow strut is subjected to first applied pressure $AP_1$ which is below the predetermined threshold. Stent 800 has a first elution rate $EP_1$ for therapeutic drug 812 when hollow strut 802 is in the first configuration. Breakable partitions $842_A$, $842_B$ sealingly contain or hold therapeutic drug 812 within respective reservoirs $840_A$, $840_B$ when hollow strut 802 is in the first configuration. When therapeutic drug 812 is contained within reservoirs $840_A$, $840_B$ via respective breakable partitions $842_A$, $842_B$, the contained therapeutic drug 812 cannot elute out of side port 804. The remaining inner surface of hollow strut 802 is not obstructed (the portion of the inner surface of hollow strut 802 that extends between breakable partitions $842_A$, $842_B$) and thus can elute out of side port 804. In the embodiment of FIG. 6, approximately 20% of the inner surface of hollow strut 802 is exposed and not obstructed while approximately 80% of the inner surface (within reservoirs $840_A$, $840_B$) is obstructed.

FIG. 10 is a cross-sectional view of hollow strut 802 being in a second configuration that is similar to the first configuration described above with respect to FIG. 5 in which the hollow strut is subjected to second applied pressure $AP_2$ which is above the predetermined threshold. Stent 800 has a second elution rate $EP_2$ for therapeutic drug 812 when hollow strut 802 is in the second configuration. The second elution rate $EP_2$ is relatively faster than the first elution rate $EP_1$. As hollow strut 802 deforms from the first configuration to the second configuration due to the higher applied pressure above the predetermined threshold, the deformation of hollow strut 802 exerts a compressive load on breakable partitions $842_A$, $842_B$ that causes them to fracture, buckle, crack, or otherwise break. As shown by directional arrows 846 on FIG. 10, therapeutic drug 812 previously contained within reservoirs $842_A$, $842_B$ is now released through cracks in breakable partitions $842_A$, $842_B$ into lumenal space 803 and then may elute through side port 804. Although described herein as being configured to break upon exertion of a compressive load or force, breakable partitions $842_A$, $842_B$ may be configured to break upon exertion of other forces such as tension or torsional forces that may be applied by a variety of medical devices including but not limited to extravascular balloons.

Although FIGS. 8-10 illustrate therapeutic substance or drug 112 as fluid that fills or partially fills reservoirs $840_A$, $840_B$, therapeutic substance or drug 112 could also be disposed within reservoirs $840_A$, $840_B$ as a coating on an inner surface of the hollow strut as shown in FIG. 3. In addition, although only two configurations of hollow strut 802 are described herein with two corresponding elution rates for the embodiment of FIGS. 8-10, additional intermediate configurations of hollow strut 802 with corresponding intermediate elution rates are possible. Stated another way, hollow strut 802 may be configured to deform in a step-wise manner between the first configuration of FIG. 9 and the second configuration of FIG. 10 in order to interpolate the elution rate in a corresponding step-wise manner between the first elution rate $EP_1$ and the second elution rate $EP_2$. For example, hollow strut 802 may be configured to deform in a step-wise manner to slowly but continually increase the number of cracks in breakable partitions $842_A$, $842_B$. Higher applied pressure(s) result in additional cracks in breakable partitions $842_A$, $842_B$ and therefore release higher amounts of therapeutic drug 812 into lumenal space 803 for elution through side port 804. For example, hollow strut 102 may be configured to deform upon exertion of applied pressures between 12.1 and 15 atm and further deform to the second configuration upon exertion of applied pressure between 15 and 18 atm, thereby increasing the number of cracks in breakable partitions $842_A$, $842_B$ at the higher applied pressure value. As such, additional configurations of hollow strut 802 and corresponding elution rates are contemplated.

FIGS. 11-12A illustrate another embodiment of a stent 1100 having a hollow strut 1102 configured to predictably deform in order to achieve different elution rates. More particularly, FIG. 11 is a perspective view of hollow strut 1102 for forming stent 1100. The construction of stent 1100 and construction of hollow strut 1102 is similar to the construction of stent 100 and hollow strut 102, respectively. Stent 1100 includes at least one side port 1104 for eluting a therapeutic drug 1112 disposed within a lumenal space 1103 of hollow strut 1102 that forms the stent. Further, similar to hollow strut 102, hollow strut 1102 is formed from an outer layer 1120 and an inner layer 1122 (best shown in FIGS. 11A and 12A) and two opposing weakened areas $1124_A$, $1126_B$ (also shown in FIGS. 11A and 12A) which have a second or relatively thinner wall thickness. However, in this embodiment, the pillars are not present and rather side port 1104 has an elongated slot configuration that changes shape as hollow strut 1102 deforms in order to increase the amount of therapeutic drug 1112 that elutes there-through. Side port 1104 having the elongated slot configuration is herein referred to as side port 1104 or slot 1104. Slot 1104 dictates or controls the amount of therapeutic drug 1112 that is elutable there-though because the slot widens as hollow strut 1102 deforms to release more therapeutic drug 1112 and thereby result in faster elution rates. By altering the amount of therapeutic drug 1112 that can elute out of slot 1104, the elution rate of stent 1100 can be tailored to suit the individual needs of the patient. In general, larger amounts of therapeutic drug 1112 being elutable out of slot 1104 generally permit a faster elution rate and smaller amounts of therapeutic drug 1112 being elutable out of slot 1104 generally provide a slower elution rate.

More particularly, FIG. 11 is a perspective view of hollow strut 1102 being in a first configuration that is similar to the first configuration described above with respect to FIG. 4 in which the hollow strut is subjected to first applied pressure $AP_1$ which is below the predetermined threshold. FIG. 11A is a cross-sectional view taken along line A-A of FIG. 11. Slot 1104 has a first width $W_1$ when hollow strut 1102 is in the first configuration, and stent 1100 has a first elution rate $EP_1$ for therapeutic drug 1112 when slot 1104 has first width $W_1$. FIG. 12 is a perspective view of hollow strut 1102 being in a second configuration that is similar to the first configuration described above with respect to FIG. 5 in which the hollow strut is subjected to second applied pressure $AP_2$ which is above the predetermined threshold. FIG. 12A is a cross-sectional view taken along line A-A of FIG. 12. Stent 1100 has a second elution rate $EP_2$ for therapeutic drug 1112 when hollow strut 1102 is in the second configuration. The second elution rate $EP_2$ is relatively faster than the first elution rate $EP_1$. As hollow strut 1102 deforms from the first configuration to the second configuration due to the higher applied pressure above the predetermined threshold, the deformation of hollow strut 1102 widens slot 1104 to a second or wider width W2 which permits larger amounts of therapeutic drug 1112 to elute through slot 1104.

Although FIGS. 11-12A illustrate therapeutic drug 1112 disposed within lumenal space 1103 of hollow strut 1102 as a coating on an inner surface of the hollow strut, therapeutic drug 1112 could also fill or partially fill the lumenal space as shown in FIG. 2A. In addition, although only two configurations of hollow strut 1102 are described herein with two corresponding elution rates for the embodiment of FIGS. 11-12A, additional intermediate configurations of hollow strut 1102 with corresponding intermediate elution rates are possible. Stated another way, hollow strut 1102 may be configured to deform in a step-wise manner between the first configuration of FIGS. 11, 11A and the second configuration of FIGS. 12, 12A in order to interpolate the elution rate in a corresponding step-wise manner between the first elution rate $EP_1$ and the second elution rate $EP_2$. For example, hollow strut 1102 may be configured to deform in a step-wise manner to slowly but continually widen slot 1104. Higher applied pressure(s) result in wider dimensions of the slot and therefore higher amounts of therapeutic drug 1112 for elution through slot 1104. For example, hollow strut 1102 may be configured to deform upon exertion of applied pressures between 12.1 and 15 atm and further deform to the second configuration upon exertion of applied pressure between 15 and 18 atm, thereby increasing the width of slot 1104 at the higher applied pressure value. As such, additional configurations of hollow strut 1102 and corresponding elution rates are contemplated.

Figure 13:
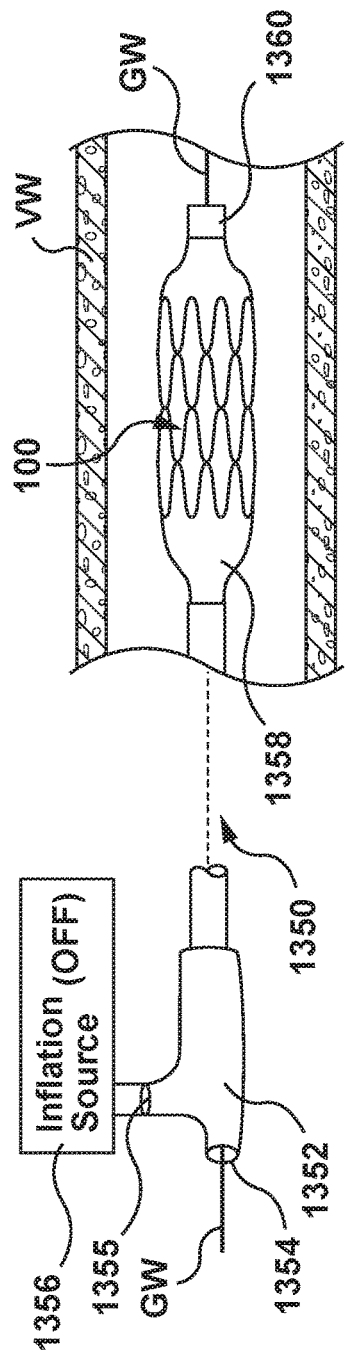
FIG. 13 illustrates a step of a method of customizing an elution rate of the drug eluting stent of FIG. 1, wherein a balloon catheter is percutaneously advanced through a vasculature, the balloon catheter having the drug-eluting stent of FIG. 1 mounted thereon, wherein the stent is in a radially compressed configuration during delivery through the vasculature.
Figure 14:
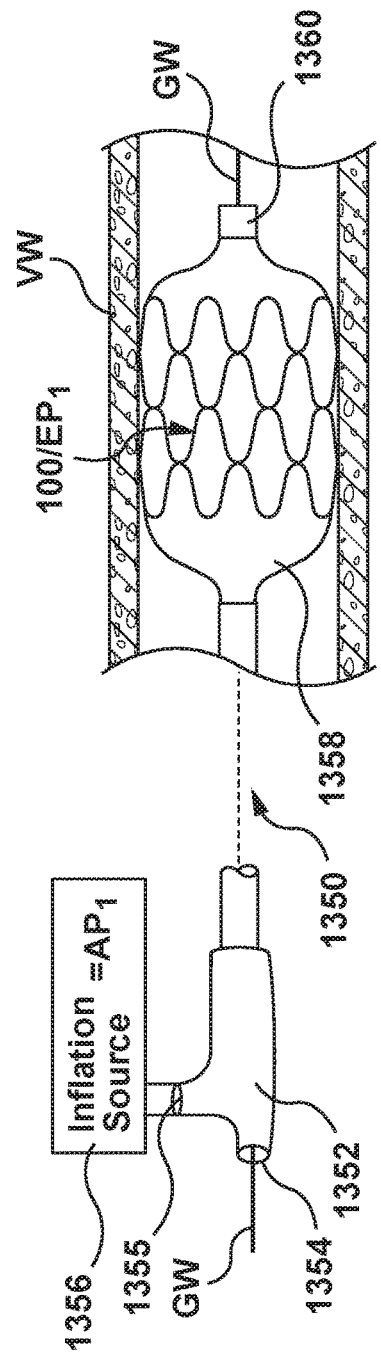
FIG. 14 illustrates a step of a method of customizing an elution rate of the drug eluting stent of FIG. 1, wherein the stent of FIG. 1 is radially expanded to a radially expanded configuration at a treatment site by inflating the balloon with the first applied pressure of FIG. 4 such that the stent has the first elution rate.
Figure 15:
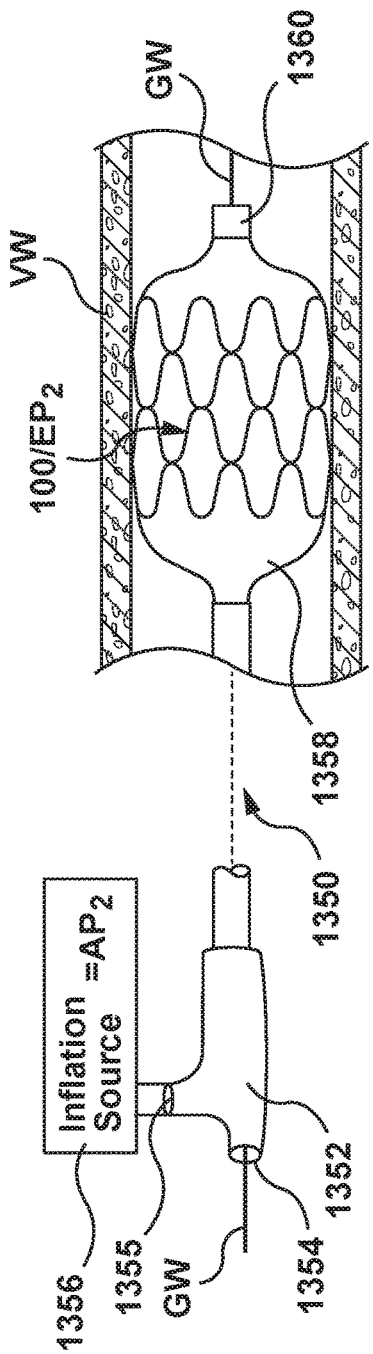
FIG. 15 illustrates a step of a method of customizing an elution rate of the drug eluting stent of FIG. 1, wherein the stent of FIG. 1 is radially expanded to a radially expanded configuration at a treatment site by inflating the balloon with the second applied pressure of FIG. 5 such that the stent has the second elution rate.

FIGS. 13-15 illustrate a method of customizing an elution rate of stent 100. FIG. 13 illustrates a balloon catheter 1350 being percutaneously advanced through a vasculature to a treatment site. Balloon catheter 1350 has stent 100 mounted on a balloon 1358 of the balloon catheter proximal to a distal end 1360 of the balloon catheter, and stent 100 is in a radially compressed configuration during delivery through the vasculature. In the depicted embodiment, balloon catheter 1350 has an over-the-wire configuration as known in the art although any conventional balloon catheter may be used including those having a rapid-exchange configuration. Balloon catheter 1350 includes a hub 1352 at the proximal end thereof, and hub 1352 extends out of the patient during clinical use. Hub 1352 includes an inflation port 1355 for coupling to a source of inflation fluid (hereinafter "inflation source 1356"). Inflation port 1355 fluidly communicates with balloon 1358 via an inflation lumen (not shown) of the balloon catheter. In addition, hub 1352 includes a guidewire port 1354 that communicates with a guidewire lumen (not shown) of the balloon catheter for receiving a guidewire GW there through. Stent 100 formed in accordance with an embodiment of the present invention is positioned over balloon 1358, although this method may also be utilized for deploying stent 800 and stent 1100. If desired, a sheath (not shown) may be provided to surround stent 100 to facilitate tracking of balloon catheter 1350 over guidewire GW through the vasculature to a treatment site. Deployment of stent 100 is accomplished by threading balloon catheter 1350 through the vascular system of the patient until stent 100 is located within treatment site, for example, a lesion which may include plaque obstructing the flow of blood through the vessel.

Once positioned, inflation source 1356 is connected to inflation port 1355 of hub 1352 so that balloon 1358 may be inflated to expand stent 100 as is known to one of ordinary skill in the art. Prior to inflating balloon 1358, a physician customizes the elution rate of stent 100 by selecting between first (or relatively slower) elution rate $EP_1$ and second (or relatively faster) elution rate $EP_2$. As described herein, the first and second elution rates are dependent upon an applied pressure exerted on hollow strut 102 of stent 100 such that the first elution rate $EP_1$ corresponds to a first configuration of hollow strut 102 and the second elution rate $EP_2$ corresponds to a second configuration of hollow strut 102. Hollow strut 102 is configured to deform from the first configuration to the second configuration when the applied pressure is above a predetermined threshold.

Stent 100 is radially expanded to a radially expanded configuration at a treatment site by inflating the balloon with an applied pressure. The applied pressure value depends upon whether the first or second elution rate is selected. When the first elution rate $EP_1$ is selected, the applied pressure is below the predetermined threshold. When the second elution rate $EP_2$ is selected, the applied pressure is above the predetermined threshold. FIG. 14 illustrates inflating balloon 1358 with the first applied pressure $AP_1$ such that stent 100 has the first elution rate $EP_1$ (and hollow strut 102 thus has the first configuration of FIG. 4), and FIG. 15 illustrates inflating balloon 1358 with the second applied pressure $AP_2$ such that stent 100 has the second elution rate $EP_2$ (and hollow strut 102 thus has the second configuration of FIG. 5). Regardless of whether stent 100 is expanded with the first applied pressure $AP_1$ or the second applied pressure $AP_2$, balloon 1358 is inflated to an extent such that stent 100 is expanded or deployed against the vascular wall of the vessel (labeled "VW" in FIGS. 13-15) to maintain the opening. Once the procedure is completed, inflation fluid is withdrawn in order to deflate balloon 1358 and balloon catheter 1350 may be retracted from the patient, leaving stent 100 implanted within the patient at the treatment site.

For all methods of customizing an elution profile or rate, stent 100 may be shipped with instructions for use for how the elution profile or rate thereof may be customized or tailored by the physician. The instructions for use may include known or established elution rates or profiles which have been verified by clinical and/or animal trials or mathematical models. More particularly, the instructions for use may include directives for applied pressure values and corresponding known or established elution profiles. The physician may use such directives when selecting a customized elution profile for stent 100.

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments. It will also be understood that each feature of each embodiment discussed herein, and of each reference cited herein, can be used in combination with the features of any other embodiment. Furthermore, there is no intention to be bound by any expressed or implied theory presented in the preceding technical field, background, brief summary or the detailed description. All patents and publications discussed herein are incorporated by reference herein in their entirety.

What is claimed is:

1. A stent having a radially compressed configuration for delivery within a vasculature and a radially expanded configuration for deployment within a body lumen, the stent comprising:
   a hollow strut that forms the stent, the hollow strut defining a lumenal space, wherein when the stent is in the radially expanded configuration the hollow strut is deformable from a first configuration to a second configuration, the second configuration being flattened relative to the first configuration;

a drug formulation disposed within the lumenal space of the hollow strut; and at least one side port for eluting the drug formulation in vivo, wherein flattening of the hollow strut from the first configuration to the second configuration increases an amount of exposed drug formulation within the lumenal space of the hollow strut such that when the hollow strut is in the first configuration there is a first exposed amount of drug formulation and when the hollow strut is in the second configuration there is a second exposed amount of drug formulation, the second exposed amount being greater than the first exposed amount, and wherein the stent has a first elution rate for the drug formulation when the hollow strut is in the first configuration and the stent has a second elution rate for the drug formulation when the hollow strut is in the second configuration, the second elution rate being faster than the first elution rate.

2. The stent of claim 1, wherein the hollow strut includes at least one weakened area configured to permit the hollow strut to deform from the first configuration to the second configuration upon application of an applied pressure above a predetermined threshold.

3. The stent of claim 2, wherein the at least one weakened area is a relatively thinner portion of the hollow strut.

4. The stent of claim 3, wherein the at least one weakened area includes two weakened areas disposed on opposing sides of the outer layer of the hollow strut.

5. The stent of claim 1, further comprising:
a first raised pillar disposed on the inner surface of the hollow strut; and
a second raised pillar disposed on the inner surface of the hollow strut, wherein the first and second raised pillars are disposed adjacent to each other when the hollow strut is in the first configuration such that there is the first exposed amount of drug formulation and wherein the first and second raised pillars are spaced apart from each other when the hollow strut is in the second configuration such that there is the second exposed amount of drug formulation.

6. The stent of claim 1, wherein the at least one side port is a slot having a first width when the hollow strut is in the first configuration and a second width when the hollow strut is in the second configuration, the second width being greater than the first width.

7. The stent of claim 1, wherein the drug formulation is disposed within opposing reservoirs formed within the lumenal space of the hollow strut, each reservoir being formed by a breakable partition disposed within the lumenal space of the hollow strut.

8. The stent of claim 7, wherein the breakable partitions are formed by a brittle layer of a material selected from the drug formulation or a biodegradable polymer.

9. The stent of claim 7, wherein the breakable partitions are configured to break upon application of an applied pressure above a predetermined threshold.

10. A stent having a radially compressed configuration for delivery within a vasculature and a radially expanded configuration for deployment within a body lumen, the stent comprising:
a hollow strut that forms the stent, the hollow strut defining a lumenal space;
a drug formulation disposed within the lumenal space of the hollow strut; and
at least one side port for eluting the drug formulation in vivo,
wherein when the stent is in the radially expanded configuration the hollow strut is deformable from a first configuration that has a first elution rate for the drug formulation to a second configuration that has a second elution rate for the drug formulation, the second elution rate being faster than the first elution rate and the second configuration being flattened relative to the first configuration, and wherein the hollow strut deforms from the first configuration to the second configuration upon application of an applied pressure above a predetermined threshold, and
wherein flattening of the hollow strut from the first configuration to the second configuration increases an amount of exposed drug formulation within the lumenal space of the hollow strut such that when the hollow strut is in the first configuration there is a first exposed amount of drug formulation and when the hollow strut is in the second configuration there is a second exposed amount of drug formulation, the second exposed amount being greater than the first exposed amount.

11. The stent of claim 10, wherein the hollow strut includes at least one weakened area configured to permit the hollow strut to deform from the first configuration to the second configuration.

12. The stent of claim 11, wherein the at least one weakened area is a relatively thinner portion of the hollow strut.

13. The stent of claim 12, wherein the at least one weakened area includes two weakened areas disposed on opposing sides of the outer layer of the hollow strut.

14. The stent of claim 10, further comprising:
a first raised pillar disposed on the inner surface of the hollow strut; and
a second raised pillar disposed on the inner surface of the hollow strut, wherein the first and second raised pillars are disposed adjacent to each other when the hollow strut is in the first configuration such that there is the first exposed amount of drug formulation and wherein the first and second raised pillars are spaced apart from each other when the hollow strut is in the second configuration such that there is the second exposed amount of drug formulation.

15. The stent of claim 10, wherein the at least one side port is a slot having a first width when the hollow strut is in the first configuration and a second width when the hollow strut is in the second configuration, the second width being greater than the first width.

16. The stent of claim 10, wherein the drug formulation is disposed within opposing reservoirs formed within the lumenal space of the hollow strut, each reservoir being formed by a breakable partition disposed within the lumenal space of the hollow strut.

17. The stent of claim 16, wherein the breakable partitions are formed by a brittle layer of a material selected from the drug formulation or a biodegradable polymer.

18. The stent of claim 16, wherein the breakable partitions are configured to break upon application of the applied pressure above the predetermined threshold.

19. A method of customizing an elution rate of a stent, the method comprising the steps of:
percutaneously advancing a balloon catheter through a vasculature, the balloon catheter having the stent mounted on a balloon of the balloon catheter, wherein the stent is in a radially compressed configuration during delivery through the vasculature and the stent includes at least one side port for eluting a drug formulation disposed within a lumenal space of a hollow strut that forms the stent; and selecting a first elution rate or a second elution rate for the drug formulation in order to customize an elution rate of the stent, the second elution rate being faster than the first elution rate, wherein the first and second elution rates are dependent upon an applied pressure exerted on the hollow strut of the stent such that the first elution rate corresponds to a first configuration of the hollow strut and the second elution rate corresponds to a second configuration of the hollow strut, the second configuration being flattened relative to the first configuration, the hollow strut being configured to deform from the first configuration to the second configuration when the applied pressure is above a predetermined threshold, and wherein flattening of the hollow strut from the first configuration to the second configuration increases an amount of exposed drug formulation within the lumenal space of the hollow strut such that when the hollow strut is in the first configuration there is a first exposed amount of drug formulation and when the hollow strut is in the second configuration there is a second exposed amount of drug formulation, the second exposed amount being greater than the first exposed amount.

20. The method of claim 19, further comprising the step of:

radially expanding the stent to a radially expanded configuration at a treatment site by inflating the balloon with an applied pressure, wherein the applied pressure is below the predetermined threshold when the first elution rate is selected and the applied pressure is above the predetermined threshold when the second elution rate is selected.

* * * * *